| United States Patent [19] | [11] Patent Number: 5,068,341 |
| Poetsch et al. | [45] Date of Patent: Nov. 26, 1991 |

[54] OPTICALLY ACTIVE HYDANTOINS

[75] Inventors: Eike Poetsch, Mühltal; Michael Casutt, Pfungstadt, both of Fed. Rep. of Germany

[73] Assignee: Merck Patent Gesellschaft Mit Beschrankter Haftung, Darmstadt, Fed. Rep. of Germany

[21] Appl. No.: 402,289

[22] Filed: Sep. 5, 1989

Related U.S. Application Data

[63] Continuation of Ser. No. 39,341, Apr. 17, 1987, abandoned.

[30] Foreign Application Priority Data

Apr. 19, 1986 [DE] Fed. Rep. of Germany ....... 3613246
Feb. 7, 1987 [DE] Fed. Rep. of Germany ....... 3703871

[51] Int. Cl.$^5$ .................. C07D 498/04; C07D 513/04
[52] U.S. Cl. ..................................... 548/154; 548/147; 548/216; 548/218
[58] Field of Search ............... 548/154, 218, 147, 216

[56] References Cited

U.S. PATENT DOCUMENTS 4,772,717 9/1988 Volkmann ............................ 548/154

OTHER PUBLICATIONS

Papov, Eur. J. Med. Chem. Chim. Ther. R1, 355(1986), Abstract only.
Lalezari, J. Het. Chem. 20, 483(1983).

*Primary Examiner*—Robert Gerstl
*Attorney, Agent, or Firm*—Millen, White & Zelano

[57] ABSTRACT

Optically active hydantoins of the formula I

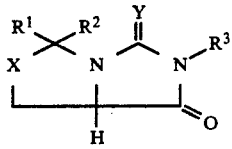

wherein X, Y, $R^1$, $R^2$ and $R^3$ have the meaning given in Patent claim 1, are useful intermediate products for the preparation of D-(+)-biotin.

8 Claims, No Drawings

OPTICALLY ACTIVE HYDANTOINS

This is a continuation of application Ser. No. 07/039,341 filed Apr. 17, 1987, now abandoned.

BACKGROUND OF THE INVENTION

This invention is co-pending with U.S. patent application Ser. No. 039,342, which disclosure is incorporated by reference herein.

The invention relates to new optically active hydantoins of the formula I:

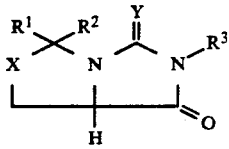

Hydrantoins of the formula I are useful starting substances for the stereospecific synthesis of D-(+)-biotin.

Processes for the stereospecific synthesis of D-(+)-biotin from sugars of suitable configuration are known. Thus, D-mannose is used as the starting material in Tetrahedron Letters No. 32, pages 2765–2766 (1975), D-glucose is used in Agric. Biol. Chem. No. 42, page 465 (1978), and D-arabinose is used as the chiral starting material in German Offenlegungsschrift 3,122,562 and German Offenlegungsschrift 3,320,140.

All these processes are characterized, however, by a high number of synthesis steps with consequently a low overall yield. The intermediate stages, which usually cannot be crystallized because of their sugar nature, are frequently obtained only in unsatisfactory purity and, because of their polyfunctionality and the associated chemical instability, require that comparatively narrow reaction parameters be observed. A number of sugars are also not accessible from natural sources, which results in a high cost.

Although the use of L-cysteine, such as is known from U.S. Pat. No. 4,009,172, U.S. Pat. No. 4,130,713 and U.S. Pat. No. 4,337,345 and Journal of the Americal Chemical Society No. 99, page 7020 (1977), avoids handling unstable intermediate stages, it gives only an unsatisfactory yield of optically active D-(+)-biotin via a total of 18 reaction stages, undesirable isomers being removed.

Substituted 3H,5H-imidazo[1,5-c]tetrahydrothiazoles, from which optically active biotin is obtained after racemate resolution, are described in another process in Journal of the Americal Chemical Society No. 105, page 5946 (1983) and in European Offenlegungsschrift 0,094,776.

Since the comparatively high number of stages, together with in some cases moderate yields and the need for optical resolution, also makes these starting substances appear to be of little use in the preparation of D-(+)-biotin, there continued to be a demand for suitable starting substances for simple, econimic and stereospecific preparation of D-(+)-biotin.

SUMMARY OF THE INVENTION

The invention was based on the object of providing new starting substances which are suitable for the preparation of optically active D-(+)-biotins without carrying out racemate resolution and without the associated need to discard or recycle the undesired enantiomer.

Upon further study of the specification and appended claims, further objects and advantages of this invention will become apparent to those skilled in the art.

It has now been found, surprisingly, that the condensed hydantoins of the formula I obtainable from the naturally occurring optically active amino acids L-cysteine, L-cystine and L-serine are outstandingly suitable for the preparation of D-(+)-biotin by a stereospecific route without additional racemate resolution.

These objects are satisfied by the provision of therefore (7R)-1H,3H-imidazo[1,5-c]azoles of the formula I

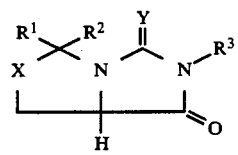

wherein
X and Y each independently of one another are O or S,
$R^1$ and $R^2$ each independently of one another are H; $C_1$–$C_8$ alkyl, wherein one or two non-adjacent $CH_2$ groups can also be substituted by O or S; $C_3$–$C_8$ cycloalkyl; $C_6$–$C_{14}$ aryl and/or $C_7$–$C_{12}$ arylalkyl which is unsubstituted or substituted by $C_1$–$C_4$ alkyl and/or $C_1$–$C_4$ alkoxy groups and/or halogen atoms and/or $C_1$–$C_4$-alkoxycarbonyl groups; $C_2$–$C_6$ alk-1-en- or alk-2-enyl; or together are $C_2$–$C_8$ alkylene, wherein one or two non-adjacent $CH_2$ groups can also be replaced by O or S,
$R^3$ is benzyl; benzyl which is substituted by one or more $C_1$–$C_4$ alkyl and/or $C_1$–$C_4$ alkoxy groups and/or halogen atoms and/or $C_1$–$C_4$ alkoxy-carbonyl groups and/or nitro groups and/or cyano groups; $C_2$–$C_6$ alk-1-en- or alk-2-enyl; $C_2$–$C_6$ alkoxyalkyl or $C_3$–$C_{16}$ alkyl and/or aryl trisubstituted silyl.

DETAILED DISCUSSION

In the above formula, X is preferably S and Y is preferably O, and particularly preferably X=S and Y=O at the same time. The radicals $R^1$ and $R^2$ are preferably H, $C_1$–$C_4$-alkyl, or phenyl or benzyl which is unsubstituted or mono- or polysubstituted by $C_1$–$C_3$ alkyl and/or alkoxy, and particularly preferably $R^1$=H and $R^2$=phenyl at the same time. The radical $R^3$ is preferably benzyl which is unsubstituted or substitued by one or more, preferably one or two, $C_1$–$C_4$ alkyl and/or $C_1$–$C_4$-alkoxy groups, particularly preferably unsubstituted benzyl, and in addition also $C_3$–$C_5$ alk-2-enyl or $C_3$–$C_{16}$ alkyl and/or aryl trisubstituted silyl. In the case of polysubstitution, preferably disubstitution, of a phenyl ring, the substituents are preferably identical, but they can also be different. They are preferably in the 4- and/or 2-position, but can also be in the 3-, 5-and/or 6-position.

Generally the alkyl portions have 1–4 C-atoms, the aryl portions 6–10 C-atoms, the cycloalkyl portions 5–7 C-atoms and the heteroaryl groups are of 1–3 rings with 4–6 C-atoms in each ring and 0, 1 or 2 hetero atoms like O, N or S in each ring.

The invention accordingly particularly relates to those compounds of the formula I in which at least one of the radicals mentioned has one of the abovementioned preferred meanings.

The invention furthermore relates to a process for the preparation of the optically active hydantoins of the formula I, characterized in that L-cysteine or L-serine is reacted with an alkali metal cyanate or thiocyanate or an alkaline earth metal cyanate or thiocyanate to give a hydantoin of the formula II

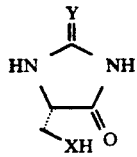                II wherein X and Y have the meaning given, this is reacted with a carbonyl compound of the formula III $R^1$—CO—$R^2$                III wherein $R^1$ and $R^2$ have the meaning given, water being split off, to give a bicyclic compound of the formula IV

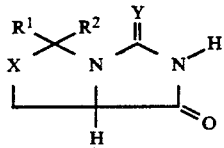                IV wherein $R^1$, $R^2$, X and Y have the meaning given, and its secondary nitrogen atom is provided with a protective group $R^3$ of the meaning given, or in that L-cysteine or L-serine is reacted with a carbonyl compound of the formula III, water being split off, to give an azolidine V

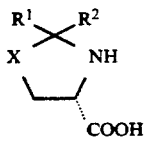                V wherein $R^1$, $R^2$ and X have the meaning given, and this is reacted with an alkali metal cyanate or thiocyanate or an alkaline earth metal cyanate or thiocyanate to give a compound of the the formula IV, and the subsequent procedure is as described above, or V is reacted with an organic isocyanate or isothiocyanate of the formula VI $R^3$—N=C=Y                VI wherein $R^3$ and Y have the meaning given above, to produce a compound of the formula I or in that L-cystine is reacted with an alkali metal cyanate or thiocyanate or an alkaline earth metal cyanate or thiocyanate to give a bishydantoin of the formula VII

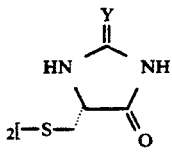                VII wherein Y is O or S, this is converted into a hydantoin of the formula II by a reducing agent and the subsequent product II is reacted as described above, or its nitrogen atom in the 3-position is provided with a protective group $R^3$ with the meaning given, and the resulting bishydantoin of the formula VIII

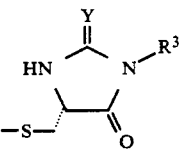                VIII wherein $R^3$ and Y have the meaning given, after cleavage by a reducing agent, is reacted with a carbonyl compound of the formula III, or L-cystine is reacted with an organic isocyanate or isothiocyanate of the formula VI given to give a bishydantoin of the formula VIII and the subsequent procedure is as described above.

The preparation of the compounds of the formula I is moreover carried out by methods which are known per se, such as are described in the literature (for example in standard works, such as Houben-Weyl, Methoden der Organischen Chemie (Methods of Organic Chemistry), Georg-Thieme-Verlag, Verlag, Stuttgart), and in particular under reaction conditions such as are known and suitable for the reactions mentioned. It is also possible for variants which are known per se and are not described here in more detail to be utilized.

The starting substances of the formula II are known or can be prepared from L-cysteine or L-serine by known methods, such as are described, for example, in Schoeberl, Hamm, Chem. Ber, 81 [1948], 210 and Karabinos, Szabo, J. Amer. Chem. Soc. 66[1944], 649, by reacting with each other the free amino acids or acid addition salts thereof with an alkali metal cyanate or thiocyanate or an alkaline earth metal cyanate or thiocyanate in a suitable solvent, such as water, alcohols or mixtures thereof, preferably at elevated temperature, and cyclizing the resulting intermediate product in situ, under the influence of an acid, for example a mineral acid.

The reaction of the hydantoins of the formula II with carbonyl compounds of the formula III to give the bicyclic compounds of the formula IV can be carried out by the known processes customary for acetalization reactions, such as are described, for example, in Houben-Weyl, Methoden der Organischen Chemie (Methods of Organic Chemistry), Volume VI/3, page 199. The reaction components are preferably reacted with the addition of a hydrating agent, such as, for example, an acid, such as sulfuric acid, phosphoric acid, hydrogen chloride or p-toluene-sulfonic acid, an acid derivative, such as phosphorus pentoxide, phosphorus trichloride, phosphorus pentachloride or phosphorus oxychloride, a metal salt, such as anhydrous calcium chloride, copper sulfate or iron(III) chloride, an acid ion exchanger or molecular sieves. The water of reaction formed can also be removed by azeotropic distillation with a suitable solvent, such as benzene, toluene, chloroform or methylene chloride. Finally, it is also possible to use, instead of a free carbonyl compound of the formula III, the acetal thereof with a suitable alcohol, preferably a lower alcohol, for the preparation of the compounds of the formula IV. The alcohol liberated in the reaction is preferably removed continuously from the reaction mixture, for example by distillation or adsorption. Water of reaction formed can also be removed by an excess of the acetal of the oxo compound III.

One equivalent of carbonyl compound III or acetal thereof, which can simultaneously be used as the solvent, is advantageously used for the reaction with the hydantoins of the formula II. However, it is preferable to add an additional inert solvent. Preferred suitable inert solvents are hydrocarbons, such as pentane, hexane, cyclohexane, benzene, toluene or xylene, and chlorinated hydrocarbons, such as methylene chloride, chloroform or carbon tetrachloride.

To protect the free nitrogen atom in the bicyclic compounds of the formula IV, these are reacted with a reactive compound which carries the radical $R^3$, with the abovementioned meaning, to give the (7R)-1H,3H-imidazo[1,5-c]azoles of the formula I. Examples of suitable compounds are benzyl chloride, benzyl bromide, 4-methoxy-benzyl benzyl chloride, 3,4-dimethoxybenzyl chloride, 4-methyl-benzyl benzyl chloride, benzyl tosylate, allyl bromide, methallyl bromide, crotyl bromide, chlorodimethyl ether, trimethyl-chlorosilane, tert.-butyldimethylchlorosilane or tert.-butyldiphenylchlorosilane. The reaction conditions for introduction of the protective groups correspond to known processes, such as are to be found, for example, in Mac Omie, Protective Groups in Organic Chemistry, Plenum Press, New York, 1973.

The reaction components are preferably reacted in a suitable solvent with the addition of a basic reagent. Particularly suitable solvents are, in particular, ethers, such as diethyl ether, di-n-butyl ether, tetrahydrofuran, dioxane or anisole, ketones, such as acetone, butanone or cyclohexanone, amides, such as dimethylformamide or phosphoric acid hexamethyltriamide, hydrocarbons, such as benzene, toluene or xylene, halogenohydrocarbons, such as carbon tetrachloride or tetrachloroethylene, and sulfoxides, such as diomethyl sulfoxide or sulfolane.

A preferred reaction procedure is the reaction of a bicyclic compound of the formula IV with a reactive compound which carries the radical $R^3$, preferably in a basic medium, bases which are of importance being, in particular, alkali metal hydroxides, such as sodium hydroxide or potassium hydroxide, alkali metal carbonates or bicarbonates, such as sodium carbonate, sodium bicarbonate, potassium carbonate or potassium bicarbonate, alkali metal acetates, such as sodium acetate or potassium acetate, alkaline earth metal hydroxides, such as calcium hydroxide, alkali metal hydrides, such as sodium hydride, amides, such as sodium methylate, sodium ethylate or lithium ethylate, or organic bases, such as triethylamine, pyridine, lutidine, collidine or quinoline.

The reaction temperature is usually between $-50°$ C. and $+250°$ C., preferably between $-20°$ C. and $+80°$ C. At these temperatures, the reactions are as a rule ended after 15 minutes to 48 hours.

In another process for the preparation of the compounds of the formula II, L-cysteine of L-serine is reacted with a carbonyl compound of the formula III to give an azolidine V. Compounds of the formula V and processes for their preparation are known, for example, from Schubert, J. Biol. Chem. 114 (1936), 341, Uskovic et al., J. Amer. Chem. Soc. 97 (1975), 5936, Lieberman et al., ibid. 70 (1948), 3094 and U.S. Pat. No. 3,957,794 and U.S. Pat. No. 4,009,172. The reaction conditions described for the preparation of the compounds of the formula IV are likewise suitable.

Azolidines of the formula V can be converted into compounds of the formula IV by means of alkali metal or alkaline earth metal cyanates or thiocyanates under the reaction conditions already described for the preparation of compounds of the formula II, and these can be further converted into the imidazo[1,5-azoles of the formula I as described.

However, it is preferable for the azoles of the formula V to be reacted with an organic isocyanate or isothiocyanate of the formula VI directly to give the imidazo[1,5-c]azoles of the formula I. Organic isocyanates and isothiocyanates of the formula VI are known or can be obtained by known methods, such as are described, for example, in Houben-Weyl, Methoden der Organischen Chemie (Methods of Organic Chemistry), Volumes VIII, page 75 and IX, page 773.

The reaction of hydantoins with phenyl isocyanate and methyl isocyanate is known from Lieberman, J. Amer. Chem. Soc. 70 (1948), 3094 and Crabb et al., Tetrahedron 29 (1973), 3389. The reaction of the azoles of the formula V with the organic isocyanates or isothiocyanates of the formula VI can also be carried out by these methods. The reaction compounds are preferably reacted in a suitable solvent, such as, for example, ethers, such as diethyl ether, di-n-butyl ether, tetrahydrofuran, dioxane or anisole, ketones, such as acetone, butanone or cyclohexanone, amides, such as dimethylformamide or phosphoric acid hexamethyltriamide, hydrocarbons, such as benzene, toluene chloride or tetrachloroethylene, and sulfoxides, such as dimethyl sulfoxide or sulfolane. Basic solvents, such as pyridine, lutidine, collidine, diethylamine or triethylamine, and mixtures of these bases with the abovementioned solvents are also suitable.

If appropriate, it may be preferable for the carbamoyl or thiocarbonmoyl compound primarily formed to be isolated and to be cyclized in a separate reaction step, water being split off. Examples of suitable dehydrating agents are acids, such as sulfuric acid, hydrogen chloride or toluenesulfonic acid, or bases, such as sodium hydroxide or potassium hydroxide. The reaction here can be carried out in the presence or absence of an inert solvent at temperatures between about 0° C. and 150° C., preferably between about 20° C. and 100° C.; examples of possible solvents are water and alcohols, such as methanol, ethanol, isopropanol or butanol.

In a further process for the preparation of the compounds of the formula II, L-cystine is reacted with an alkali metal cyanate or thiocyanate or an alkaline earth metal cyanate or thiocyanate to give a bishydantoin of the formula VII. The same methods as have already been described for the preparation of the hydantoins of the formula II can be used for this, the same or similar reaction conditions being applied.

The bishyantoins of the formula VII can be treated with a reducing agent to give hydantoins of the formula II (X=S), from which the imidazo[1,5-c]thiazoles of the formula I (X=S) are prepared by the methods described above. Suitable reducing agents can be found, for example, in Houben-Weyl, Methoden der Organischen Chemie (Methods of Organic Chemistry), Volume 15/1, page 798. Sodium/liquid ammonia, zinc/acid or phosphonium iodide are preferably suitable for reductive cleavage of the disulfide bond. The reduction of the bishydantoins of the formula VII is preferably carried out with one equivalent, but in particular with an excess, of reducing agent in a suitable solvent which matches the chemical nature of the reagent, such as, for example, water, liquid ammonia, alcohols, such as methanol, ethanol or isopropanol, acids, such as hydrochloric acid, sulfuric acid, formic acid or acetic acid, ethers, such as diethyl ether, tetrahydrofuran or dioxane, or mixtures thereof, preferably at temperatures between about −50° C. and +150° C.

A particularly advantageous process for the cleavage of the disulfide bond in the compound of the formula VII comprises thiolysis thereof with a suitable mercaptan, such as, for example, thiophenol, butane-1,4-dithiol or 1,4-dithio-threitol, by a procedure analogous to that described by Hase and Walter, Inst. J. Pept. Prot. Res. 5 (1973), 283. The reaction components are preferably reacted in a suitable solvent, such as, for example, aqueous alkali metal hydroxide solutions, chlorohydrocarbons carbons or liquid ammonia, at temperatures between about −40° C. and +120° C.

The bishydantoins of the formula VII can furthermore be provided with a protective group of the formula $R^3$. The methods already described for the preparation of the compounds of the formula I from the bicyclic compounds of the formula IV can be used for the preparation of these protected bishydantoins of the formula VIII, the same or similar reaction conditions being applied.

Another process for the preparation of the protected bishydantoins of the formula VIII comprises reacting L-cystine with an organic isocyanate or isothiocyanate of the above formula VI analogously to the preparation of compounds of the formula I from azolidines of the formula V, processes the same as or similar to those already described for the preparation of the compounds of the formula I being used.

To convert the compounds of the formula VIII into the (7aR)-1H,3H-imidazol[1,5-c]thiazoles of the formula I (X=S), these are treated with a reducing agent or a reagent which effects thiolysis in a manner corresponding to that for the preparation of the hydantoins of the formula II from the disulfides of the formula VIII, using the same or similar processes and reaction conditions, and the products are then reacted with a carbonyl compound of the formula III in a manner corresponding to the preparation of compounds of the formula V.

The (7aR)-1H-3H-imidazo[1,5-c]azoles of the formula I according to the invention are useful intermediate products for the stereospecific preparation of D-(+)-biotin, such as is described, for example, in DE-A 13613246 equivalent to the U.S. application incorporated by reference above. In such preparation:

a) I is reduced to an alcohol of the formula IX

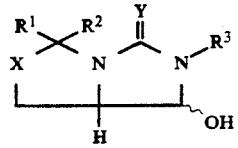
IX wherein $R^1$, $R^2$, $R^3$ X and Y have the meaning given, this is converted into an activated ester of the formula X

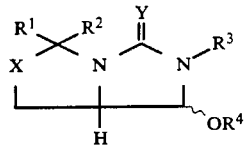
X wherein $R^1$, $R^2$, $R^3$, X and Y have the meaning given and the radical $R^4$ is an activating ester group. This compound is reacted with an alkali metal cyanate or a cyanosilane or alkaline earth metal cyanide to give a nitrile of the formula XI

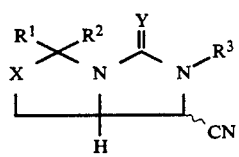
XI wherein $R^1$, $R^2$, $R^3$, X and Y have the meaning given, this is reacted with a base or an acid to give an acid derivative of the formula XII

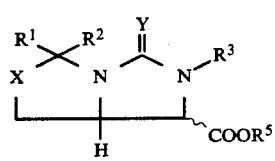
XII wherein $R^1$, $R^2$, $R^3$, X and Y have the meaning given and $R^5$ is H, lower alkyl, cycloalkyl or aryl. This is cyclized, water being split off, to give a lactone of the formula XIII

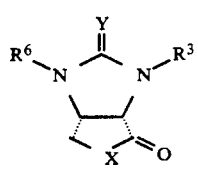
XIII wherein $R^3$, X and Y have the meaning given and $R^6$ is H or $R^1R^2CH$, this is converted by known processes into D-(+)-biotin or by a procedure in which b) XI is reacted with an organometallic compound to give an oxo compound of the formula XIV

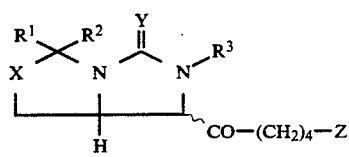
XIV wherein $R^1$, $R^2$, $R^3$, X and Y have the meaning given and Z is $OR^5$ or $COOR^5$, this is split by treatment with an acid and/or a reducing agent to given an imidazolidine of the formula XV

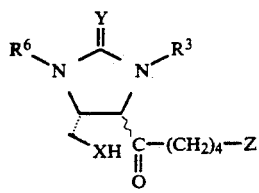

wherein $R^3$, $R^6$, X, Y and Z have the meaning given, this is cyclized, under the action of a base to give a biotin derivative of the formula XVI

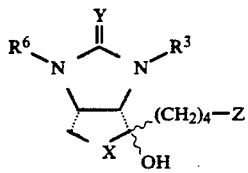

wherein $R^3$, $R^6$, X, Y, and X have the meaning given, and this is converted into D-(+)-biotin by known processes, or by a procedure in which c) XI is reacted with a reducing agent to give an aldehyde of the formula XVII

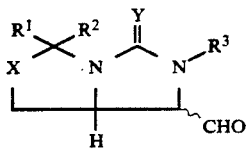

wherein $R^1$, $R^2$, $R^3$, X and Y have the meaning given, this is condensed with an organophosphorous compound to give an unsaturated carboxylic acid of the formula XVIII

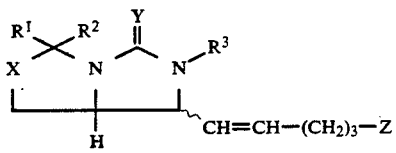

wherein $R^1$, $R^2$, $R^3$, X, Y and Z have the meaning given, this is converted by an acid and/or a reducing agent into a biotin derivative of the formula XIX

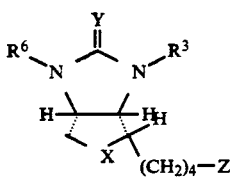

wherein $R^3$, $R^6$, X, Y, and Z have the meaning given, and this is converted into D-(+)-biotin by known processes, or by a procedure in which d) an oxo compound of the formula XIV given above is converted, under the action of an acid to a biotin derivative of the formula XX

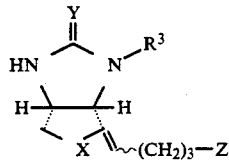

wherein $R^3$, X, Y, and Z have the meaning given, and this is converted into D-(+)-biotin by known processes.

The full discloses of any references and applications mentioned above and below are hereby incorporated by reference.

The following examples are intended to illustrate the invention without limiting it.

Without further elaboration, it is believed that one skilled in the art can, using the preceding description utilize the present invention to its fullest extent. The following preferred specific embodiments are, therefore, to e construed as merely illustrative, and not limitative of the remainder of the disclosure in any way whatsoever.

In the following examples, all temperatures are set forth uncorrected in degrees Celsius; unless otherwise indicated, all parts and percentages are by weight.

EXAMPLE 1

102.31 g (0.7 mol) of L-cysteinhydantoin (Karabinos, Szabo, J. Am. Chem. Soc. 66 [1944], 649) are suspended in 1,000 ml of toluene, and 74.28 g (0.7 mol) of benzaldehyde are added.

107.33 g (0.7 mol) of phosphoryl chloride are added dropwise at 0° C. in the course of 30 minutes, the mixture is stirred at room temperature for a further 12 hours and the precipitate is filtered off with suction and rinsed with 400 ml of toluene in portions. The residue is recrystallized from methanol. 141.7 g of (7aR)-3-phenyl-1H,3H-imidazo[1,5-c]thiazole-5,7(6H,7aH)-dione with a melting point of 177°-179° C. are obtained.

$[\alpha]_{365}^{20} = -1250°$, c=1 (methanol)

The following compounds are prepared analogously:
(7aR)-3-methyl-1H,3H-imidazo[1,5-c]thiazole-5,7(6H,7aH)-dione
(7aR)-3-ethyl-1H,3H-imidazo[1,5c]thiazole-5,7(6H,7aH)-dione
(7aR)-3-cyclopentyl-1H,3H-imidazo[1,5-c]thiazole-5,7(6H, 7aH)-dione
(7aR)-3-cyclohexyl-1H,3H-imidazo[1,5-c]thiazole-5,7(6H, 7aH)-dione
(7aR)-3,3-tetramethylene-1H,3H-imidazo[1,5c]thiazole-5, 7(6H,7aH)-dione
(7aR)-3,3-pentamethylene-1H,3H-imidazo[1,5-c]thiazole-5, 7(6H,7aH)-dione
(7aR)-3-(4-methylphenyl)-1H,3H-imidazo[1,5-c]thiazole-5, 7(6H,7aH)-dione
(7aR)-3-(4-ethylphenyl)-1H,3H-imidazo[1,5-c]thiazole-5, 7(6H,7aH)-dione
(7aR)-3-(4-methoxyphenyl)-1H,3H-imidazo[1,5-c]thiazole-5, 7(6H,7aH)-dione
(7aR)-3-(4-ethoxyphenyl)-1H,3H-imidazo[1,5-c]thiazole-5, 7(6H,7aH)-dione
(7aR)-3-phenyl-1H,3H-imidazo[1,5-c]thiazole-5(6H)-thion-7(7aH)-one (7aR)-3-methyl-1H,3H-imidazo[1,5-c]thiazole-5(6H)-thion-7(7aH)-one
(7aR)-3-ethyl-1H,3H-imidazo[1,5-c]thiazole-5(6H)thion-7(7aH)-one (7aR)-3-cyclopentyl-1H,3H-imidazol[1,5-c]thiazole-5(6H)-thion-7(7aH)-one
(7aR)-3-cyclohexyl-1H,3H-imidazo[1,5-c]-thiazole-5(6H)-thion-7(7aH)-one
(7aR)-3,3-tetramethylene-1H,3H-imidazo[1,5-c]thiazole-5(6H)-thion-7(7aH)-one
(7aR)-3,3-pentamethylene-1H,3H-imidazol[1,5-c]thiazole-5(6)-thion-7(7aH)-one
(7aR)-3-(4-methylphenyl)-1H,3H-imidazo[1,5-c]thiazole-5(6)-thion-7(7aH)-one
(7aR)-3-(4-ethylphenyl)-1H,3H-imidazo[1,5-c]thiazole-5(6H)-thion-7(7aH)-one
(7aR)-3-(4-methoxyphenyl)-1H,3H-imidazol[1,5-c]thiazole-5(6H)-thion-7(7aH)-one
(7aR)-3-(4-ethoxyphenyl)-1H,3H-imidazo[1,5-c]thiazole-5(6)-thion-7(7aH)-one
(7aR)-3-phenyl-1H,3H-imidazo[1,5-c]oxazole-5,7(6H,7aH)-dione
(7aR)-3-methyl-1H,3H-imidazo[1,5-c]oxazole-5,7(6H,7aH)-dione
(7aR)-3-ethyl-1H,3H-imidazo[1,5-c]oxazole-5,7(6H,7aH)-dione
(7aR)-3-cyclopentyl-1H,3H-imidazo[1,5-c]oxazole-5,7(6H, 7aH)-dione
(7aR)-3-cyclohexyl-1H,3H-imidazo[1,5c]oxazole-5,7(6H, 7aH)-dione
(7aR)-3,3-tetramethylene-1H,3H-imidazo[1,5-c]oxazole-5, 7(6H,7aH)-dione
(7aR)-3,3-pentamethylene-1H,3H-imidazo[1,5-oxazole-5, 7(6H,7aH)-dione
(7aR)-3-(4-methylphenyl)-1H,3H-imidazo[1,5-c]oxazole-5, 7(6H,7aH)-dione
(7aR)-3-(4-ethylphenyl)-1H,3H-imidazo[1,5-c]oxazole-5,7(6H, 7aH)-dione
(7aR)-3-(4-methoxyphenyl)-1H,3H-imidazo[1,5-cycloxazole-5, 7(6H,7aH)-dione
(7aR)-3-(4-ethoxyphenyl)-1H,3H-imidazo[1,5-c]oxazole-5, 7(6H,7aH)-dione

EXAMPLE 2

46.85 g (0.2 mol) of (7aR)-3-phenyl-1,3H-imidazo-[1,5-c]thiazole-5,7(6H,7aH)-dione, dissolved in 450 ml of tetrahydrofuran, are added dropwise to a suspension of 6.6 g (0.22 mol) of 80% sodium hydride in 450 ml of tetrahydrofuran at room temperature under nitrogen. After about 30 minutes, the evolution of hydrogen has ended. 37.63 g (0.22 mol) of benzyl bromide are now added drop-wise in the course of 15 minutes, the mixture is boiled under reflux for 3 hours and most of the solvent is then distilled off.

The residue is partitioned between 500 ml of methylene chloride and 500 ml of water and the organic phase is washed twice with 100 ml of water each time, dried over sodium sulfate and concentrated under reduced pressure.

Trituration with methanol gives 59.2 g of (7aR)-3-phenyl-6-benzyl-1H,3H-imidazo[1,5-c]thiazole-5,7(6H, 7aH)-dione with a melting point of 78°-79° C.

$[\alpha]_{365}^{20} = -1020°$, c=1 (methanol)

The following compounds are prepared analogously:
(7aR)-3-phenyl-6-(4-methylbenzyl)-1H,3H-imidazo[1,5-c]-thiazole-5,7(6H,7aH)-dione
(7aR)-3-phenyl-6-(4-methoxybenzyl)-1H,3H-imidazo[1,5-c]-thiazole-5,7(6H,7aH)-dione
(7aR)-3-phenyl-6-(4-chlorobenzyl)-1H,3H-imidazo[1,5-c]-thiazole-5,7(6H,7aH)-dione
(7aR)-3-phenyl-6-(4-nitrobenzyl)-1H,3H-imidazo[1,5-c]-thiazole-5,7(6H,7aH)-dione
(7aR)-3-phenyl-6-allyl-1H,3H-imidazo[1,5-c]thiazole-5,7(6H,7aH)-dione
(7aR)-3-phenyl-6-trimethylsilyl-1-3H-imidazo[1,5-c]-thiazole-5,7(6,7aH)-dione
(7aR)-3-methyl-6-benzyl-1H,3H-imidazo[1,5-c]thiazole-5, 7(6H,7aH)-dione
(7aR)-3-methyl-6-(4-methylbenzyl)-1H,3H-imidazo[1,5-c]-thiazole-5,7(6H,7aH)-dione
(7aR)-3-methyl-6-(4-methoxybenzyl)-1H,3H-imidazo[1,5-c]-thiazole-5,7(6H,7aH)-dione
(7aR)-3-methyl-6-(4-chlorobenzyl)-1H,3H-imidazo[1,5-c]-thiazole-5,7(6H,7aH)-dione
(7aR)-3-methyl-6-(4-nitrobenzyl)-1H,3H-imidazo[1,5-c]-thiazole-5,7(6H,7aH)-dione
(7aR)-3-methyl-6-allyl-1H,3H-imidazo[1,5-c]thiazole-5, 7(6H,7aH)-dione
(7aR)-3-methyl-6-trimethylsilyl-1H,3H-imidazo[1,5-c]-thiazole-5,7(6H,7aH)-dione

EXAMPLE 3

138.19 g (1 mol) of potassium carbonate and 130.39 g (1.03 mol) of benzyl chloride are added to a solution of 234.27 g (1 mol of (7aR)-3-phenyl-1H,3H-imidazo[1,5-c]thiazole-(6,7aH)5,7-dione in 700 ml of dimethylformamide at room temperature, and the mixture is stirred for 3 hours at 50° C.

Thereafter the mixture is filtered and the filtrate concentrated under reduced pressure.

The oily residue is stirred into 950 ml of methanol and is allowed to crystallize at 0° C.

275.2 g of (7aR)-3-phenyl-6-benzyl-1H,3-imidazo-[1,5-c]thiazole-(6H,7aH)5,7-dione, with a melting point of 77°-78° C., are obtained.

$[\alpha]_{365}^{20} = -1018°$, c=1 (methanol).

The following compounds are obtained analogously:
(7aR)-3,3-pentamethylene-6-benzyl-1H,3H-imidazol[1,5-c]-thiazole-5,7(6H,7aH)-dione
(7aR)-3,3-pentamethylene-6-(4-methylbenzyl)-1H,3H-imidazo-[1,5-c]thiazole-5,7(6H,7aH)-dione
(7aR)-3,3-pentamethylene-6-(4-methoxybenzyl)-1H,3H-imidazo-[1,5-c]thiazole-5,7(6H,7aH)-dione
(7aR)-3,3-pentamethylene-b 6-(4-chlorobenzyl)-1H,3H-imidazo-[1,5-c]thiazole-5,7(6H,7aH)-dione
(7aR)-3,3-pentamethylene-6-(4-nitrobenzyl)-1H,3H-imidazo-[1,5-c]thiazole-5,7(6H,7aH)-dione
(7aR)-3,3-pentamethylene-6-allyl-1H,3H-imidazo[1,5-c]-thiazole-5,7(6H,7aH)-dione
(7aR)-3,3-pentamethylene-6-trimethylsilyl-1H,3H-imidazo-[1,5-c]thiazole-5,7(6H,7aH)-dione
(7aR)-3-phenyl-6-benzyl-1H,3H-imidazo[1,5-]thiazole-5(6)-thion-7(7aH)-one
(7aR)-3-phenyl-6-(4-methylbenzyl)-1H,3H-imidazo[1,5-c]-thiazole-5(6H)-thion-7(7aH)-one
(7aR)-3-phenyl-6-(4-methoxybenzyl)-1H,3H-imidazo[1,5-c]-thiazole-5(6H)-thion-7(7aH)-one
(7aR)-3-phenyl-6-(4-chlorobenzyl)-1H,3H-imidazo[1,5-c]-thiazole-5(6H)-thion-7(7aH)-one
(7aR)-3-phenyl-6-(4-nitrobenzyl)-1H,3H-imidazo[1,5-c]-thiazole-5(6H)-thion-7(7aH)one
(7aR)-3-phenyl-6-allyl-1H,3H-imidazo[1,5-c]thiazole-5(6H)-thion-7(7aH)-one
(7aR)-3-phenyl-6-trimethylsilyl-1H,3H-imidazo[1,5-c]-thiazole-5(6H)-thion-7(7aH)-one

EXAMPLE 4

Following the procedure described in Example 3, 234.27 g (1 mol) of (7aR)-3-phenyl-1H,3H-imidazo[1,5-c]-thiazole-(6H,7aH)5,7-dione are reacted with 176.17 g (1.03 mol) of benzylbromide and 138.19 g (1 mol) of potassium carbonate in 700 mL of dimethylformamide.

281.3 g of (7aR)-3-phenyl-6-benzyl-1H,3H-imidazo-[1,5-c]thiazole-5,7-dione, with a melting point of 77°-78° C., are obtained.

$[\alpha]_{365}^{20} = -1020°$, c=1 (methanol).

The following compounds are prepared analogously:
(7aR)-3-methyl-6-benzyl-1H,3H-imidazo[1,5-c]thiazole-5(6)-thion-7(7aH)-one
(7aR)-3-methyl-6-(4-methylbenzyl)-1H,3H-imidazo[1,5-c]-thiazole-5(6H)-thion-7(7aH)-one
(7aR)-3-methyl-6-(4-methoxybenzyl)-1H,3H-imidazo[1,5-c]-thiazole-5(6H)-thion-7(7aH)-one
(7aR)-3-methyl-6-(4-chlorobenzyl)-1H,3H-imidazo[1,5-c]-thiazole-5(6H)-thion-7(7aH)-one
(7aR)-3-methyl-6-(4-nitrobenzyl)-1H,3H-imidazo[1,5-c]-thiazole-5(6H)-thion-7(7aH)-one
(7aR)-3-methyl-6-allyl-1H,3H-imidazo[1,5-c]thiazole-5(6H)-thion-7(7aH)-one
(7aR)-3-methyl-6-trimethylsilyl-1H,3H-imidazo[1,5-c]-thiazole-5(6H)-thion-7(7aH)-one
(7aR)-3,3-pentamethylene-6-benzyl-1H,3H-imidazo[1,5-c]-thiazole-5(6H)-thion-7(7aH)-one
(7aR)-3,3-pentamethylene-6-(4-methylbenzyl)-1H,3H-imidazo-[1,5-c]thiazole-5(6H)-thion-7(7aH)-one
(7aR)-3,3-pentamethylene-6-(4-methoxybenzyl)-1H,3H-imidazo-[1,5-c]thiazole-5(6H)-thion-7(7aH)-one
(7aR)-3,3-pentamethylene-6-(4-chlorobenzyl)-1H,3H-imidazo-[1,5-c]thiazole-5(6H)-thion-7(7aH)-one
(7aR)-3,3-pentamethylene-6-(4-nitrobenzyl)-1H,3H-imidazo-[1,5-c]thiazole-5(6H)-thion-7(7aH)-one
(7aR)-3,3-pentamethylene-6-allyl-1H,3H-imidazo[1,5-c]thiazole-5(6H)-thion-7(7aH)-one
(7aR)-3,3-pentamethylene-6-thion-7(7aH)-one

EXAMPLE 5

Following the procedure described in Example 3, 234.27 g (1 mol) of (7aR)-3-phenyl-1H,3H-imidazo[1,5-c]-thiazole-5,7-dione are reacted with 130.39 g 1.03 mol) of benzyl chloride, 138.19 g (1 mol) of potassium carbonate and 14.99 g (0.1 mol) of sodium iodide in 700 ml of dimethylformamide.

288.9 g of (7aR)-3-phenyl-6-benzyl-1H,3H-imidazo-[1,5-c]thiazole-5,7-dione, with a melting point of 78°-79° C., are obtained.

$[\alpha]_{365}^{20} = 1023°$, c=1 (methanol).

The following compounds are obtained analogously:
(7aR)-3-methyl-6-benzyl-1H,3H-imidazo[1,5-c]oxazole-5, 7(6H,7aH)-dione
(7aR)-3-methyl-6-(4-methylbenzyl)-1,3H-imidazo[1,5-c]-oxazole-5,7(6H,7aH)-dione
(7aR)-3-methyl-6-(4-methoxybenzyl)-1H,3H-imidazo[1,5-c]-oxazole-5,7(6H,7aH)-dione
(7aR)-3-methyl-6-(4-chlorobenzyl)-1H,3H-imidazo[1,5-c]-oxazole-5,7(6H,7aH)-dione
(7aR)-3-methyl-6-(4-nitrobenzyl)-1H,3H-imidazo[1,5-c]-oxazole-5,7(6H,7aH)-dione
(7aR)-3-methyl-6-allyl-1H,3H-imidazo[1,5-c]oxazole-5,7-(6H,7aH)-dione
(7aR)-3-methyl-6-trimethylsilyl-1H,3H-imidazo[1,5-c]-oxazole-5,7(6H,7aH)-dione
(7aR)-3-phenyl-6-benzyl-1H,3H-imidazo[1,5-c]oxazole-5, 7(6H,7aH)-dione
(7aR)-3-phenyl-6-(4-methylbenzyl)-1H,3H-imidazo[1,5-c]-oxazole-5,7(6H,7aH)-dione
(7aR)-3-phenyl-6-(4-methoxybenzyl)-1H,3H-imidazo[1,5-c]-oxazole-5,7(6H,7aH)-dione
(7aR)-3-phenyl-6-(4-chlorobenzyl)-1,3H-imidazo[1,5-c]-oxazole-5,7(6H,7aH)-dione
(7aR)-3-phenyl-6-(4-nitrobenzyl)-1H,3H-imidazo[1,5-c]-oxazole-5,7(6H,7aH)-dione
(7aR)-3-phenyl-6-allyl-1H,3H-imidazo[1,5-c]oxazole-5,7(6H, 7aH)-dione
(7aR)-3-phenyl-6-trimethylsilyl-1H,3H-imidazol[1,5-c]-oxazole-5,7(6H,7aH)-dione
(7aR)-3,3-pentamethylene-6-benzyl-1H,3H-imidazo[1,5-c]-oxazole-5,7(6H,7aH)-dione
(7aR)-3,3-pentamethylene-6-(4-methylbenzyl)-1H,3H-imidazo-[1,5-c]oxazole-5,7(6H,7aH)-dione
(7aR)-3,3-pentamethylene-6-(4-methoxybenzyl)-1H,3H-imid-azo[1,5-c]oxazole-5,7(6H,7aH)-dione
(7aR)-3,3-pentamethylene-6-(4-chlorobenzyl)-1H,3H-imidazo[1,5-c]oxazole-5,7(6H,7aH)-dione
(7aR)-3,3-pentamethylene-6-(4-nitrobenzyl)-1H,3H-imidazo-[1,5-c]oxazole-5,7(6H,7aH)-dione
(7aR)-3,3-pentamethylene-6-allyl-1H,3H-imidazo[1,5-c]-oxazole-5,7(6H,7aH)-dione
(7aR)-3,3-pentamethylene-6-trimethylsilyl-1H,3H-imidazo-[1,5-c]oxazole-5,7(6H,7aH)-dione

EXAMPLE 6

20.93 g (0.1 mol) of (4S)-2-phenyl-thiazolidinecarboxylic acid (Confalone et al., J. Amer. Chem. Soc. 99 (1977), 7020) in 200 ml of tetrahydrofuran are taken in an apparatus under nitrogen. A solution of 16.0 g (0.12 mol) of benzyl isocyanate in 50 ml of tetrahydrofuran is added dropwise to the suspension in the course of 20 minutes and the mixture is stirred at 50° C. for one hour. It is then cooled to 0° C., 30 ml of concentrated hydrochloric acid are added and the mixture is stirred at 60° C. for 90 minutes.

Thereafter, the mixture is concentrated, the residue is partitioned between 200 ml of methylene chloride and 300 ml of water and the organic phase is washed twice with 100 ml of water each time, dried over sodium sulfate and concentrated under reduced pressure. Trituration with methanol gives 25.9 g of (7aR)-3-phenyl-6-benzyl-1H,3H-imidazo[1,5-c]thiazole-5,7(6H,7aH)-dione with a melting point of 79° C.

$[\alpha]_{365}^{20} = -1010°$, c=1 (methanol)

The following compounds are obtained analogously:
(7aR)-3-phenyl-6-(4-methylbenzyl)-1H,3H-imidazo[1,5-c]-thiazole-5,7(6H,7aH)-dione
(7aR)-3-phenyl-6-(4-methoxybenzyl)-1H,3H-imidazol[1,5-c]-thiazole-5,7(6H,7aH)-dione
(7aR)-3-phenyl-6-(4-chlorobenzyl)-1H,3H-imidazol[1,5-c]-thiazole-5,7(6H,7aH)-dione
(7aR)-3-phenyl-6-(4-nitrobenzyl)-1H,3H-imidazo[1,5-c]-thiazole-5,7(6H,7aH)-dione
(7aR)-3-phenyl-6-allyl-1H,3H-imidazo[1,5-c]thiazole-5,7(6H,7aH)-dione
(7aR)-3-phenyl-6-trimethylsilyl-1H,3H-imidazo[1,5-c]-thiazole-5,7(6H,7aH)-dione
(7aR)-3-methyl-6-benzyl-1H,3H-imidazo[1,5-c]thiazole-5,7(6H,7aH)-dione
(7aR)-3-methyl-6-(4-methylbenzyl)-1H,3H-imidazo[1,5-c]-thiazole-5,7(6H,7aH)-dione
(7aR)-3-methyl-6-(4-methoxybenzyl)-1H,3H-imidazo[1,5-c]-thiazole-5,7(6H,7aH)-dione (7aR)-3-methyl-6-(4-chlorobenzyl)-1H,3H-imidazo[1,5-c]-thiazole-5,7(6H,7aH)-dione (7aR)-3-methyl-6-(4-nitrobenzyl)-1H,3H-imidazo[1,5-c]-thiazole-5,7(6H,7aH)-dione (7aR)-3-methyl-6-allyl-1H,3H-imidazo[1,5-c]thiazole-5,7(6H,7aH)-dione (7aR)-3-methyl-6-trimethylsilyl-1H,3H-imidazo[1,5-c]-thiazole-5,7(6H,7aH)-dione (7aR)-3,3-pentamethylene-6-benzyl-1H,3H-imidazo[1,5-c]-thiazole-5,7(6H,7aH)-dione (7aR)-3,3-pentamethylene-6-(4-methylbenzyl)-1H,3H-imidazo[1,5-c]thiazole5,7(6H,7aH)-dione (7aR)-3,3-pentamethylene-6-(4-methoxybenzyl)-1H,3H-imidazo[1,5-c]thiazole-5,7(6H,7aH)-dione (7aR)-3,3-pentamethylene-6-(4-chlorobenzyl)-1H,3H-imidazo[1,5-c]thiazole-5,7(6H,7aH)-dione (7aR)-3,3-pentamethylene-6-(4-nitrobenzyl)-1,H,3H-imidazo[1,5-c]thiazole-5,7(6H,7aH)-dione (7aR)-3,3-pentamethylene-6-allyl-1H,3H-imidazo[1,5-c]-thiazole-5,7(6H,7aH)-dione (7aR)-3,3-pentamethylene-6-trimethylsilyl-1H,3H-imidazo-[1,5-c]thiazole-5,7(6H,7aH)-dione The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. An optically active hydantoin of the formula

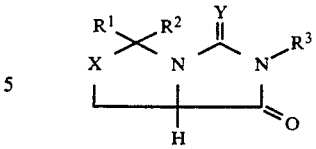

wherein

X and Y are each independently O or S;

$R^1$ and $R^2$ are each independently are H; $C_{1-8}$-alkyl, $C_{1-8}$-alkyl wherein one or two non-adjacent $CH_2$ groups can also be substituted by O or S; $C_{3-8}$ cycloalkyl; $C_{6-14}$ aryl; $C_{7-12}$-arylalkyl; $C_{6-14}$ aryl or $C_{1-12}$-arylalkyl each substituted by $C_{1-4}$ alkyl, $C_{1-4}$ alkoxy, halogen, or $C_{1-4}$-alkoxycarbonyl; $C_{2-6}$ alk-1-enyl; $C_{2-6}$ alk-2-enyl; or $R^1$ and $R^2$ together are $C_{2-8}$ alkylene, or $C_{2-8}$-alkylene wherein one or two non-adjacent $CH_2$ groups is replaced by O or S, is benzyl; benzyl substituted by one or more of $C_{1-4}$-alkyl, $C_{1-4}$-alkoxy, halogen, $C_{1-4}$-alkoxycarbonyl, nitro or cyano; $C_{2-6}$ alk-1-enyl; $C_{2-6}$ alk-2-enyl; $C_{2-6}$ alkoxyalkyl; $C_{3-16}$ tri(alkyl and/or aryl)silyl.

2. A compound according to claim 1, wherein X is S and Y is O.

3. A compound according to claim 1, wherein $R^1$ and $R^2$ are each independently H; $C_{1-4}$-alkyl; phenyl, benzyl or phenyl or benzyl each substituted by $C_{1-3}$-alkyl or by $C_{1-3}$-alkoxy.

4. A compound according to claim 3, wherein $R^1$ is H and $R^2$ is phenyl.

5. A compound according to claim 3, wherein $R^3$ is benzyl; benzyl substituted by $C_{1-3}$-alkyl or by $C_{1-4}$-alkoxy; $C_{3-5}$-alk-2-enyl; $C_{3-16}$ trialkylsilyl or $C_{3-16}$-triarylsilyl.

6. A compound according to claim 5, wherein $R^3$ is benzyl.

7. A compound according to claim 1, wherein $R^1$ or $R^2$ is 2,4-disubstituted phenyl.

8. A compound according to claim 1, wherein $R^3$ is 2,4-disubstituted benzyl.

* * * * *

UNITED STATES PATENT AND TRADEMARK OFFICE
CERTIFICATE OF CORRECTION

PATENT NO. : 5,068,341

DATED : November 26, 1991

INVENTOR(S) : Poetsch et al.

It is certified that error appears in the above-identified patent and that said Letters Patent is hereby corrected as shown below:

Col. 16; Claim 1, Lines 11-13:

Delete - - -

( $C_{1-8}$-alkyl, $C_{1-8}$-alkyl wherein one or two non-adjacent $CH_2$ groups can also be substituted by O or S; )

Col. 16: Claim 1, Lines 18 and 19:

Delete - - -

( or two non-adjacent) Delete (s) from group

Col. 16; Claim 1, Line 19 :

Insert - - - " or $R^2$ is also $C_{1-8}$-alkyl wherein
after S,   " one or two non-adjacent $CH_2$ groups
           " is substituted by O or S; and"

Col. 16 Claim 1, Line 22: Insert "or" after ";"

Col. 16 Claim 1, Line 23  Delete ($C_{3-16}$ tri(alkyl and/or aryl)siyl.)

UNITED STATES PATENT AND TRADEMARK OFFICE
CERTIFICATE OF CORRECTION

PATENT NO. : 5,068,341

DATED : November 26, 1991

INVENTOR(S) : Poetsch et al

It is certified that error appears in the above-identified patent and that said Letters Patent is hereby corrected as shown below:

Col. 16; Claim 5, Line 33: Insert "or" after ";"
Col. 16; Claim 5 Line 34: Delete ( $C_{3-16}$ trialkylsilyl or $C_{3-16}$ triarylsilyl. )

Signed and Sealed this

Twentieth Day of April, 1993

*Attest:*

MICHAEL K. KIRK

*Attesting Officer*  *Acting Commissioner of Patents and Trademarks*